(12) United States Patent
Smulko et al.

(10) Patent No.: US 7,680,607 B1
(45) Date of Patent: Mar. 16, 2010

(54) SYSTEM AND METHOD FOR GAS RECOGNITION BY ANALYSIS OF BISPECTRUM FUNCTIONS

(75) Inventors: Janusz Smulko, Suchy Dwor (PL); Laszlo B. Kish, College Station, TX (US); Gabor Schmera, San Diego, CA (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 1227 days.

(21) Appl. No.: 11/134,597

(22) Filed: May 12, 2005

Related U.S. Application Data

(60) Provisional application No. 60/570,966, filed on May 13, 2004.

(51) Int. Cl.
*G01N 31/00* (2006.01)
(52) U.S. Cl. .............................. 702/22; 702/23; 702/24; 702/27; 702/30; 702/32; 422/83; 422/98; 436/149; 73/23.2; 73/23.21
(58) Field of Classification Search ................. 436/150; 702/27; 422/56–58
See application file for complete search history.

(56) References Cited

OTHER PUBLICATIONS

Smulko et al., On the statistical analysis of noise in chemical sensors and its application for sensing, 2001, World Scientific Publishing Company, p. L147-L153.*

Jurs et al., Computational methods for the analysis of chemical snesor array data from volatile analytes, Jun. 7, 2000, American Chemical Society, Chem. Rev. 2000, 100, p. 2649-2678.*

J. M. Smulko, L. B. Kish & Gabor Schmera, "Application of Nonlinearity Measures to Chemical Sensor Signals," Proc. of SPIE vol. 5115 (2003) p. 92-100.

* cited by examiner

*Primary Examiner*—Tony G Soohoo
*Assistant Examiner*—Robert Eom
(74) *Attorney, Agent, or Firm*—Kyle Eppele; Arthur K. Samora

(57) ABSTRACT

A System and Method for Gas Recognition by Analysis of Bispectrum Functions is based on the Higher-Order Spectral analysis of time series measurements of resistance fluctuations in Metal Oxide Semiconductor (MOS) gas sensors, such as Taguchi-type sensors. A two-dimensional contour plot module of the bispectrum function is treated as a pattern. These patterns include information about the analyte(s) whereby characteristics of the gas can be identified.

6 Claims, 5 Drawing Sheets

SYSTEM AND METHOD FOR GAS RECOGNITION BY ANALYSIS OF BISPECTRUM FUNCTIONS

CROSS-REFERENCE TO RELATED APPLICATIONS

This application claims the benefit of U.S. Provisional Application No. 60/570,966 (Navy Case No. 96,130), filed May 13, 2004, entitled "System and Method for Gas Recognition by Analysis of Bispectrum Functions," hereby incorporated by reference.

FEDERALLY-SPONSORED RESEARCH AND DEVELOPMENT

The System and Method for Gas Recognition by Analysis of Bispectrum Functions was made with United States Government support and is available for licensing for commercial purposes. The United States Government has certain rights in this invention. Licensing and technical inquiries may be directed to the Office of Patent Counsel, Space and Naval Warfare Systems Center, San Diego, Code 20012, San Diego, Calif., 92152; telephone (619)553-3001, facsimile (619)553-3821.

BACKGROUND

The System and Method for Gas Recognition by Analysis of Bispectrum Functions generally relates to chemical analyte detection and identification, and more particularly, to a system and method of chemical analyte detection and identification by analysis of resistance fluctuations of a Metal Oxide Semiconductor (MOS) gas sensor.

Homeland defense, including anti-terrorist efforts require highly selective, sensitive, and reliable detection of harmful agents. Intensive research has resulted in the use of chemical and biological sensor elements for the development of systems known as electronic noses (for gas and odor sensing) and electronic tongues (for fluid sensing).

One way of gas sensing is based on Metal Oxide Semiconductor (MOS) gas sensors. These devices generally operate by measuring the change in resistance between electrode pairs as a result of the interaction between the surface of the metal-oxide semiconductor and the ambient gas. As gas molecules are adsorbed and desorbed by the MOS sensor, the resistance of the sensor changes. Traditionally, only the DC (average) resistance is measured. The DC resistance is a single value that cannot be used as a pattern for recognition of different gases.

More recently, the power spectral density of fluctuations in the resistance of the MOS sensor have been measured. This power spectral density can be used to generate a pattern to identify different gases by giving information about power of the stochastic component at different frequencies. However, the power spectral density looses information about the phase relationships of the resistance fluctuations.

Therefore, it can be appreciated that a sensitive and reliable method of MOS sensor analysis that preserves phase relationships of resistance fluctuations is needed.

SUMMARY

The present invention provides a System and Method for Gas Recognition by Analysis of Bispectrum Functions that addresses the problems mentioned previously.

In one aspect of the invention, a method for analyzing a chemical analyte includes the steps of: (1) generating a fluctuation output signal in response to a plurality of resistance fluctuations of a Metal Oxide Semiconductor (MOS) gas sensor; (2) transforming the fluctuation output signal into a bispectrum signal; and (3) generating an analyte output signal that identifies a characteristic of the analyte if the bispectrum signal corresponds to a characteristic of a known analyte.

In another aspect of the invention, a chemical sensor system is provided that includes a metal oxide semiconductor (MOS) gas sensor. The chemical sensor system also includes: (1) measurement means for generating a fluctuation output signal responsive a plurality of resistance fluctuations of the MOS gas sensor; (2) bispectrum means for transforming the fluctuation output signal into a bispectrum signal; (3) decision means, coupled to the bispectrum means, for generating an analyte output signal that identifies a characteristic of the chemical analyte if the bispectrum signal corresponds to a characteristic of a known analyte.

In still another aspect of the invention, a computer program product (CPP) is provided that includes a machine-readable recording medium and a first, second, and third instruction means recorded on the medium for use with a chemical sensor system that includes a metal oxide semiconductor (MOS) gas sensor. The first, second, and third instruction means are recorded on the medium for directing the chemical sensor system to: (1) generate a fluctuation output signal in response to a plurality of resistance fluctuations of the MOS gas sensor; (2) transform the fluctuation output signal into a bispectrum signal; and (3) generate an analyte output signal that identifies a characteristic of the chemical analyte if the bispectrum signal corresponds to a characteristic of a known analyte.

DETAILED DESCRIPTION

Following is a glossary of terms used to describe the System and Method for Gas Recognition by Analysis of Bispectrum Functions. The definitions set forth in the glossary are representative of the intended meanings as used herein.

GLOSSARY

The term "chemical analyte" means a substance being measured in an analytical procedure.

The term "chemical sensor" means a device that responds to chemical stimulus.

The term "machine-readable recording medium" means a physical material in or on which data may be represented wherein the data can be read by an input unit for storage, processing, or display.

The term "power spectral density" means the power distribution of a signal with respect to frequency.

Figure 1:
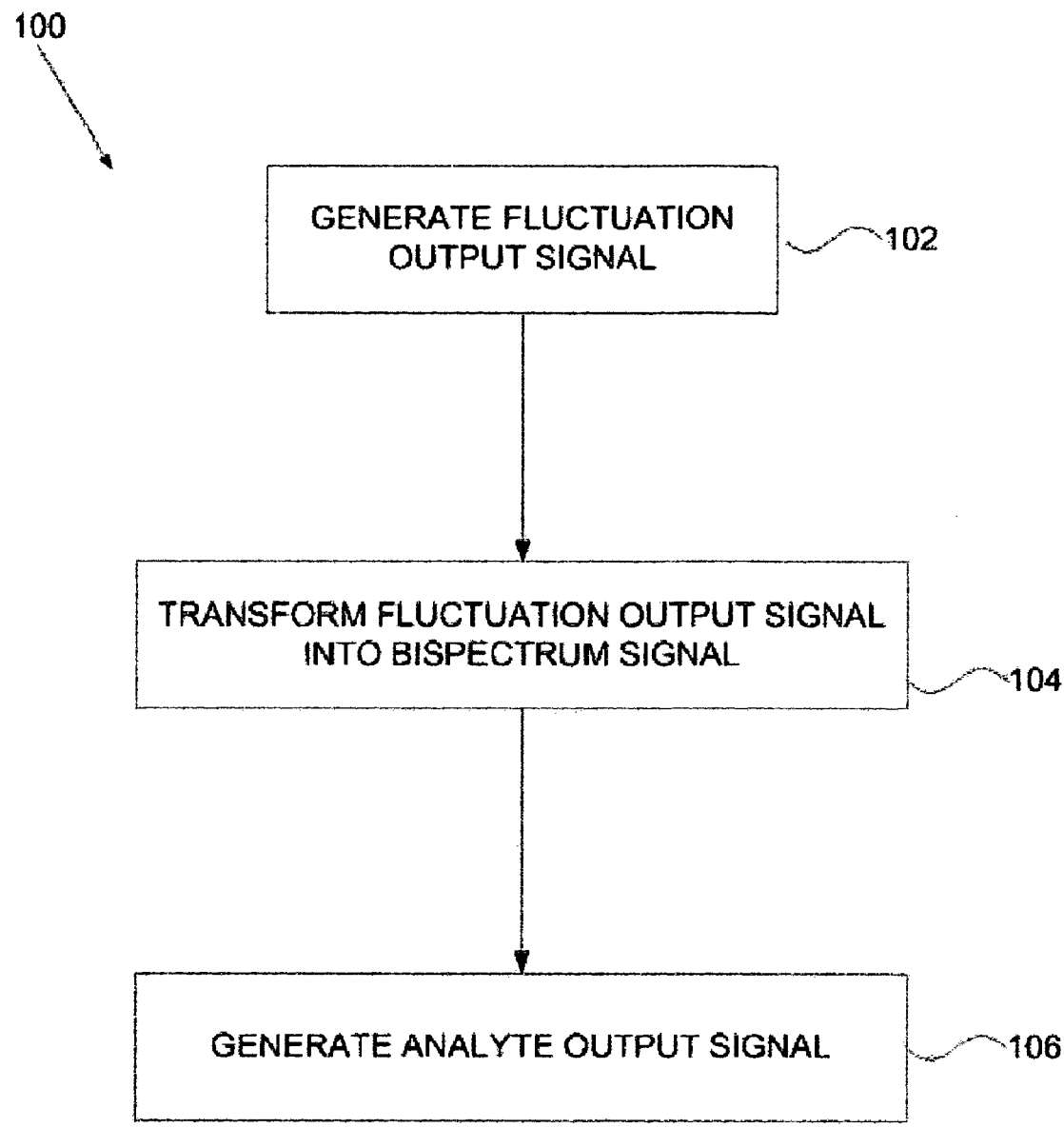
FIG. 1 is a flow-chart of a method of analyzing a chemical analyte, in accordance with the System and Method for Gas Recognition by Analysis of Bispectrum Functions.

FIG. 1 illustrates a method 100, in accordance with the System and Method for Gas Recognition by Analysis of Bispectrum Functions. Method 100 utilizes higher-order spectral analysis of time series measurements of resistance fluctuations in a Metal Oxide Semiconductor (MOS) gas sensor. By way of example, the MOS gas sensor may be a Taguchi-type sensor, including the commercially available sensors RS 286-636 (designed for detection of carbon dioxide) and RS 286-642 (designed for detection of nitrogen oxide).

Taguchi-type sensors are surface active, grainy, $SnO_2$-based semiconductor film gas sensors working at elevated temperatures. The sensor signal is the mean value of the resistance and the spontaneous resistance fluctuations around the mean value, influenced by ambient gas. According to simple models, the sensor's DC resistance is dominated by the potential barrier at grain boundaries that prevents carriers from moving freely. The barrier is formed when the metal oxide crystal is heated in air and oxygen is adsorbed with a negative charge on the crystal surface. The barrier height is reduced when the concentration of oxygen ions decreases in the presence of deoxidizing gas. As a result, the DC resistance decreases.

Method 100 includes step 102 for generating a fluctuation output signal in response to resistance fluctuations of a Metal Oxide Semiconductor (MOS) gas sensor. This fluctuation output signal represents a normalized time series of the fluctuations in resistance of the gas sensor.

Step 104 transforms the fluctuation output signal into a bispectrum signal. Step 104 includes subtracting, from the fluctuation output signal, its mean value. All samples of the time series are then divided by their standard deviation. The bispectrum function of the normalized time series is then calculated by two-dimensional fast Fourier transform according to a bispectrum function. The bispectrum function, being the function of two frequencies f1 and f2, is defined by:

$$S_{3x}(f_1, f_2) = \sum_{k=-\infty}^{\infty} \sum_{l=-\infty}^{\infty} C_{3x}(k, l) e^{-j2\pi f_1 k} e^{-j2\pi f_2 l}, \quad \text{EQ. 1}$$

where $C_{3x}(k,l) = E[x(n)x(n+k)x(n+l)]$ is the third-order cummulant of the zero-mean process $x(n)$.

The bispectrum function is equal to zero for processes with zero skewness, i.e. for Gaussian processes. Bispectrum of two statistically independent random processes equals the sum of the bispectrums of the individual random processes. This implies that Gaussian components in the recorded noise will be eliminated and non-Gaussian signals will be drawn out of Gaussian noise when the bispectrum function is used for analysis. This is also valid for Gaussian noise having 1/f-like power spectral density.

Figure 3:
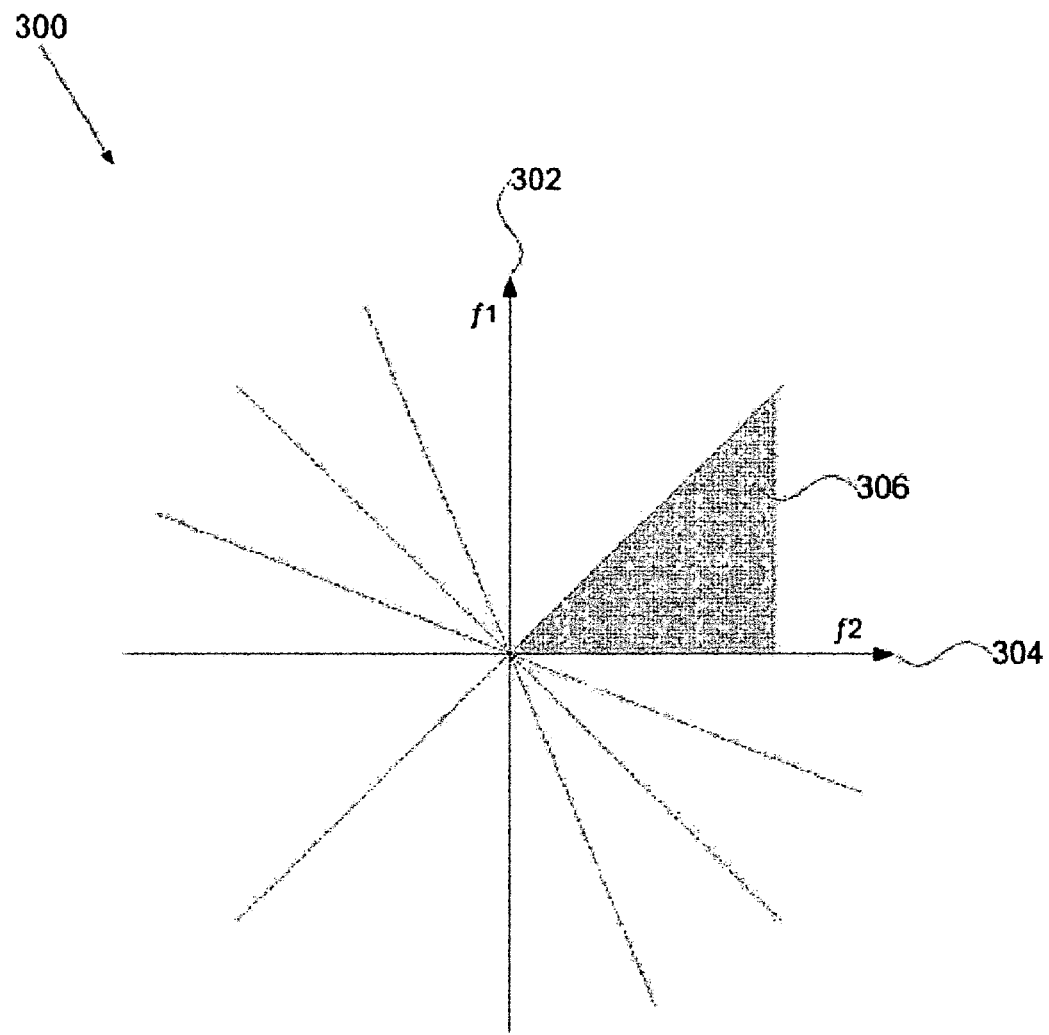
FIG. 3 is a graph of a bispectrum function, in accordance with the System and Method for Gas Recognition by Analysis of Bispectrum Functions.

The definition of bispectrum function EQ. 1 suggests the existence of axial symmetries for stationary random signals, as shown in FIG. 3. Values on the shaded region 306 of the frequency plane (defined by frequencies 302 and 304) determine the entire function.

Step 106 includes generating an analyte output signal that identifies a characteristic of an analyte if the bispectrum signal corresponds to a characteristic of a known analyte. By way of example, a computer may be used for housing a database of bispectrum patterns from previously measured analytes. If the bispectrum signal matches a pattern in the patterns database, the computer may generate an analyte output signal that represents a characteristic of the analyte, such as identification or quantification of the analyte.

Figure 4:
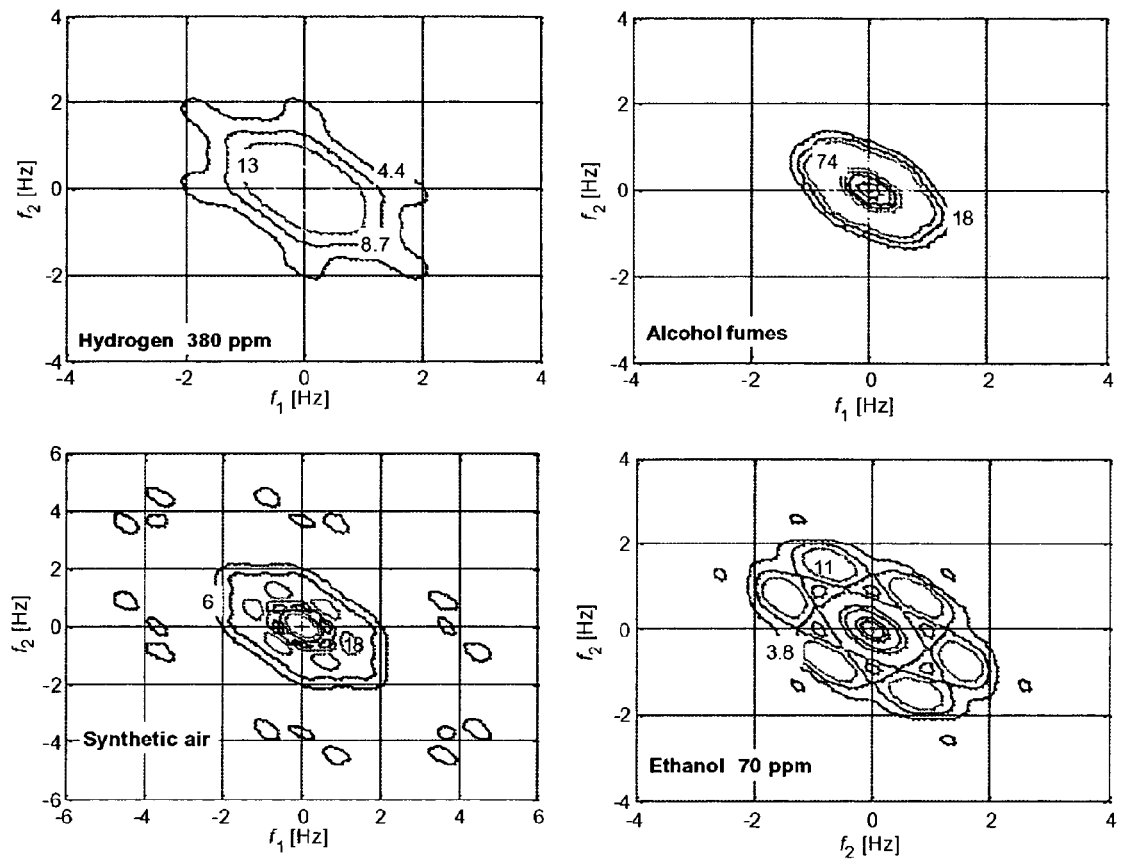
FIG. 4 is a series of graphs showing the bispectrum plots for a variety of gases, in accordance with the System and Method for Gas Recognition by Analysis of Bispectrum Functions.

Experimental results confirm the presence of characteristic non-linear components in the registered time series when the MOS gas sensor is exposed to different gases. The contour plots (FIG. 4) of the bispectrum were obtained by plotting contour (level-crossing) lines at N levels of bispectrum function value. The level values are calculated by dividing the maximum value of bispectrum function by N. The resultant bispectrum functions were shaped significantly differently for the measured gas samples, as shown in FIG. 4 (the bispectrum plots at sampling frequency fs=100 Hz when a MOS sensor was exposed to different gases). This characteristic property of the bispectrum function can be used to identify the gas samples, thereby significantly improve the selectivity of the sensing process.

Figure 2:
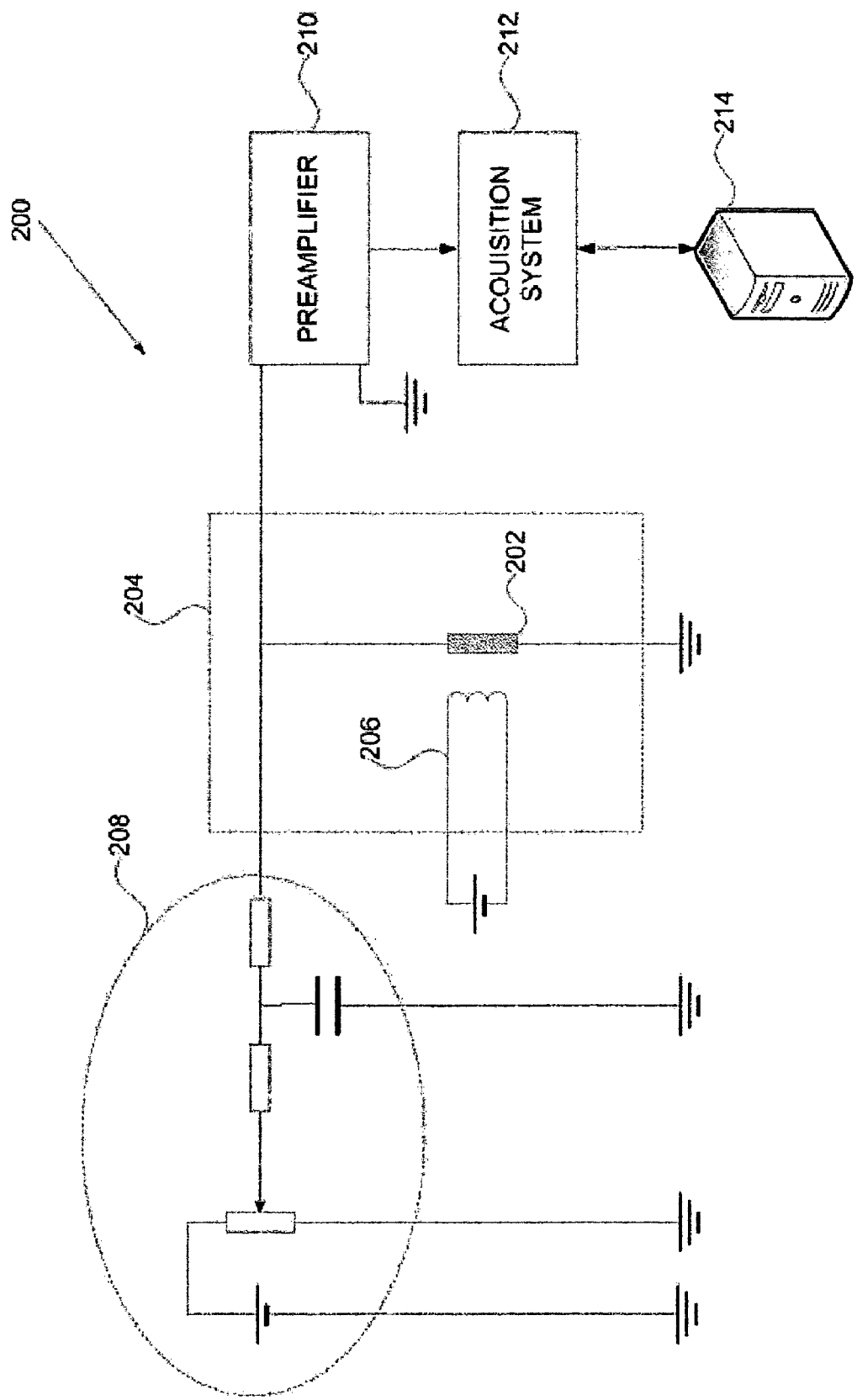
FIG. 2 is a block diagram of a chemical sensor system, in accordance with the System and Method for Gas Recognition by Analysis of Bispectrum Functions.

FIG. 2 illustrates a chemical sensor system 200, in accordance with the System and Method for Gas Recognition by Analysis of Bispectrum Functions. Sensor system 200 includes a MOS gas sensor 202 and optional heater 206, both housed inside a sensor chamber 204. By way of example, sensor chamber 204 may be made of stainless steel. MOS gas sensor 202 may be a Taguchi-type sensor, including the commercially available sensors RS 286-636 (designed for detection of carbon dioxide) and RS 286-642 (designed for detection of nitrogen oxide).

MOS gas sensor 202 is connected to biasing circuitry 208. Although FIG. 2 shows a particular arrangement of biasing circuitry 208, it is recognized that any such circuitry that allows for the creation of a voltage potential across MOS gas sensor 202 that is directly proportional to the resistance of gas sensor 202 may be utilized. Spontaneous fluctuations around the mean value of the resistance of sensor 202 occur as gas is introduced into sensor chamber 204. These fluctuations in resistance cause fluctuations in the voltage potential across sensor 202.

Included in sensor system 200 is measurement means, which is represented in FIG. 2 as preamplifier 210. Preamplifier 210 may comprise any suitable amplifier, such as a Stanford Instruments SR560 preamplifier. Preamplifier 210 is coupled to sensor 202 and generates a fluctuation output signal x(t) that is responsive to the resistance fluctuations of sensor 202.

Sensor system 200 also includes bispectrum means for transforming the fluctuation output signal x(t) into a bispectrum signal. FIG. 2 shows an example of bispectrum means as acquisition system 212, which may include an ADInstruments PowerLab/4Sp Data Acquisition system.

Acquisition system 212 normalizes the fluctuation output signal x(t) and subtracts its mean value. All samples of the time series are divided by its standard deviation. The bispectrum function of the normalized time series is then calculated by two-dimensional fast Fourier transform according to a bispectrum function. The bispectrum function, being the function of two frequencies f1 and f2, is defined by:

$$S_{3x}(f_1, f_2) = \sum_{k=-\infty}^{\infty} \sum_{l=-\infty}^{\infty} C_{3x}(k, l) e^{-j2\pi f_1 k} e^{-j2\pi f_2 l},  \quad \text{EQ. 1}$$

where $C_{3x}(k,l) = E[x(n)x(n+k)x(n+l)]$ is the third-order cummulant of the zero-mean process $x(n)$.

The bispectrum function is equal to zero for processes with zero skewness, i.e. for Gaussian processes. Bispectrum of two statistically independent random processes equals the sum of the bispectrums of the individual random processes. This implies that Gaussian components in the recorded noise will be eliminated and non-Gaussian signals will be drawn out of Gaussian noise when the bispectrum function is used for analysis. This is also valid for Gaussian noise having 1/f -like power spectral density.

The definition of bispectrum function EQ. 1 suggests the existence of axial symmetries for stationary random signals, as shown in FIG. 3. Values on the shaded region 306 of the frequency plane (defined by frequencies 302 and 304) determine the entire function.

Sensor system 200 also include decision means for generating an analyte output signal that identifies a characteristic of the gas or chemical analyte. Decision means is represented in FIG. 2 as computer 214. Computer 214 receives the bispectrum signal and identifies a characteristic of the analyte measured by matching the bispectrum signal to a patterns database of previously measured analytes. If the bispectrum signal matches a pattern in the patterns database, computer 214 generates an analyte output signal that represents the characteristic, such as identification or quantification of the analyte.

Experimental results confirm the presence of characteristic non-linear components in the registered time series when the sensor 202 was exposed to different gases. The contour plots (FIG. 4) of the bispectrum were obtained by plotting contour (level-crossing) lines at N levels of bispectrum function value. The level values are calculated by dividing the maximum value of bispectrum function by N. The resultant bispectrum functions were shaped significantly differently for the measured gas samples, as shown in FIG. 4 (the bispectrum plots at sampling frequency fs=100 Hz when sensor 202 was exposed to different gases). This characteristic property of the bispectrum function can be used to identify the gas samples, thereby significantly improve the selectivity of the sensing process.

Figure 5:
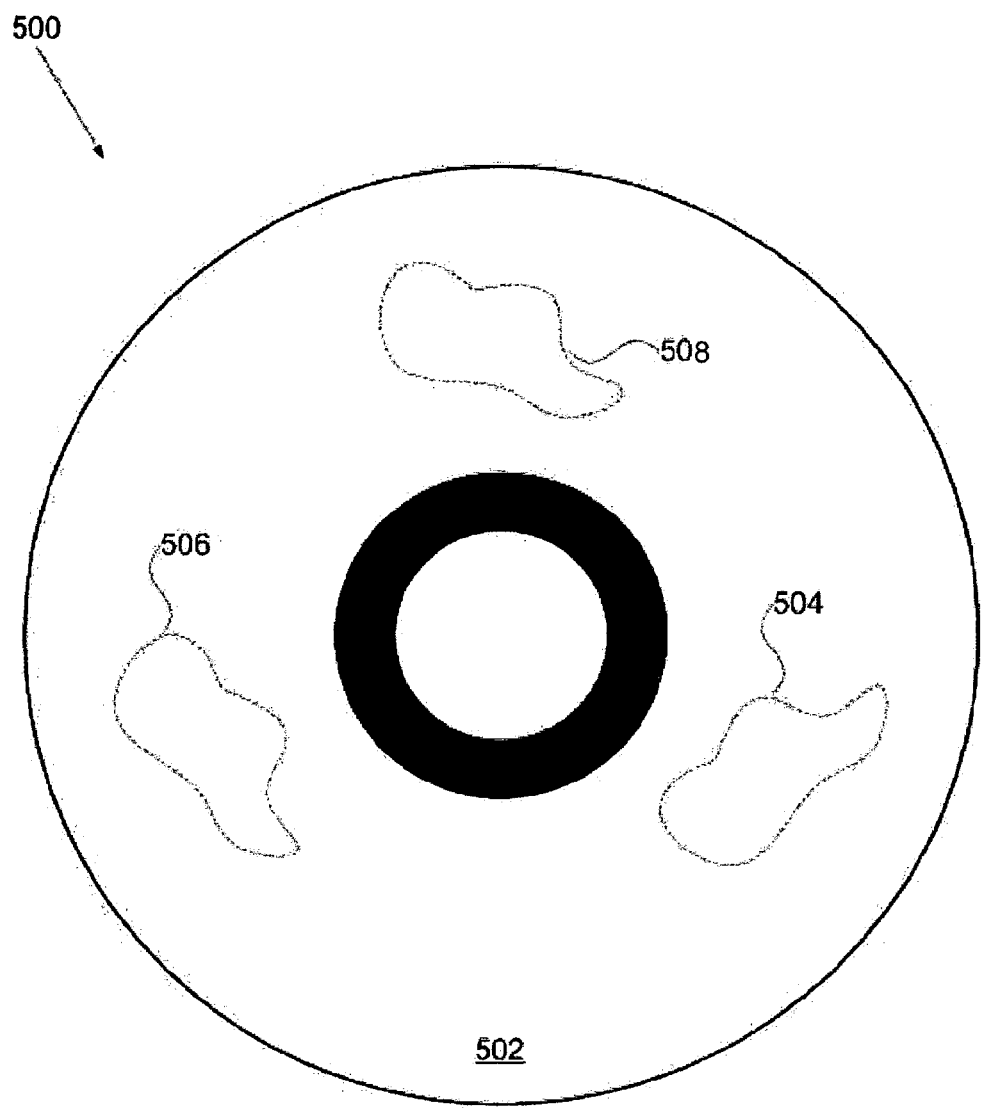
FIG. 5 is a computer program product, in accordance with the System and Method for Gas Recognition by Analysis of Bispectrum Functions.

FIG. 5 illustrates a computer program product (CPP) 500, in accordance with the System and Method for Gas Recognition by Analysis of Bispectrum Functions. CPP 500 is for use with a chemical sensor system including a metal oxide semiconductor (MOS) gas sensor. CPP 500 includes a machine-readable recording medium 502 and a first, second, and third instruction means, recorded on the recording medium 502.

First instruction means 504 are for directing the chemical sensor system to generate a fluctuation output signal in response to a plurality of resistance fluctuations of the MOS gas sensor. By way of example, the MOS gas sensor may be a Taguchi-type sensor, including the commercially available sensors RS 286-636 (designed for detection of carbon dioxide) and RS 286-642 (designed for detection of nitrogen oxide). These sensors generate a signal that is the mean value of the resistance and the spontaneous resistance fluctuations around the mean value, influenced by ambient gas. The fluctuation output signal represents a normalized time series of these resistance fluctuations.

Second instruction means 506 are for directing the chemical sensor system to transform the fluctuation output signal into a bispectrum signal. The mean value is subtracted from the fluctuation output signal and all of the samples of the time series are divided by their standard deviation. The bispectrum function of the normalized time series is then calculated by two-dimensional fast Fourier transform according to a bispectrum function. The bispectrum function, being the function of two frequencies f1 and f2, is defined by:

$$S_{3x}(f_1, f_2) = \sum_{k=-\infty}^{\infty} \sum_{l=-\infty}^{\infty} C_{3x}(k, l) e^{-j2\pi f_1 k} e^{-j2\pi f_2 l},  \quad \text{EQ. 1}$$

where $C_{3x}(k,l) = E[x(n)x(n+k)x(n+l)]$ is the third-order cummulant of the zero-mean process $x(n)$.

Third instruction means 508 are for directing the chemical sensor system to generate an analyte output signal that identifies a characteristic of the analyte detected if the bispectrum signal corresponds to a characteristic of a known analyte. By way of example, a patterns database may be recorded on recording medium 502 for storing bispectrum patterns from previously measured analytes. If the bispectrum signal matches a pattern in the patterns database, the sensor system may generate an analyte output signal that represents a characteristic of the analyte, such as identification or quantification of the analyte.

We claim:

1. A method of analyzing a chemical analyte, said method consisting of the steps of:

generating a fluctuation output signal in response to a plurality of resistance fluctuations of a Metal Oxide Semiconductor (MOS) gas sensor;

adjusting current flow through said sensor using a biasing circuit to achieve current differentials sufficient to detect different analytes, and sufficient for obtaining a measurement of said fluctuation output signal;

normalizing said measurement of said fluctuation output signal for current differentials by dividing by the standard deviation of a time series of sampled current; and transforming said fluctuation output signal into a bispectrum signal represented by the bispectrum function $$S_{3x}(f_1, f_2) = \sum_{k=-\infty}^{\infty} \sum_{l=-\infty}^{\infty} C_{3x}(k, l) e^{-j2\pi f_1 k} e^{-j2\pi f_2 l}$$

using positive and negative values for frequencies $f_1$ and $f_2$ of said bispectrum function;

establishing a contour graph that is representative of the results of said transforming step, said contour graph created using said positive and negative values for said frequencies $f_1$ and $f_2$;

comparing said contour graph to a database of reference contour graphs, said reference contour graphs created using said positive and negative values for said frequencies $f_1$ and $f_2$ corresponding to known analytes;

generating an analyte output signal that identifies a characteristic of said analyte; and determining if said contour graph utilizing said positive and negative values for said frequencies $f_1$ and $f_2$ corresponds to one of said reference contour graphs from said database.

2. The method as in claim 1, wherein said bispectrum signal substantially represents the bispectrum function:

$$S_{3x}(f_1, f_2) = \sum_{k=-\infty}^{\infty} \sum_{l=-\infty}^{\infty} C_{3x}(k, l)e^{-j2\pi f_1 k}e^{-j2\pi f_2 l},$$

wherein $C_{3x}(k,l)$ is the third-order cummulant of the zero-mean process $x(n)$ represented substantially by the function $C_{3x}(k,l)=E[x(n)x(n+k)x(n+l)]$, where $E[\ ]$ denotes average.

3. A chemical sensor system consisting of:
a metal oxide semiconductor (MOS) gas sensor;
measurement means for generating a fluctuation output signal responsive to a plurality of resistance fluctuations of said MOS gas sensor represented as a time series of sampled current;
a biasing circuit for adjusting current flow through said sensor as is sufficient to detect different analytes;
a means for transforming said time series of sampled current into a bispectrum signal represented by the equation $$S_{3x}(f_1, f_2) = \sum_{k=-\infty}^{\infty} \sum_{l=-\infty}^{\infty} C_{3x}(k, l)e^{-j2\pi f_1 k}e^{-j2\pi f_2 l},$$

said bispectrum equation using positive and negative values for frequencies $f_1$ and $f_2$;
a graphing means for establishing a contour graph that is representative of said bispectrum signal, said contour graph using positive and negative values for said frequencies $f_1$ and $f_2$;
a means for normalizing said time series of sampled current by dividing said time series of sampled current by the standard deviation;
a database of reference contour graphs created using said positive and negative values for said frequencies $f_1$ and $f_2$ corresponding to known said bispectrum signals, which further correspond to known said analytes; and,
a decision means, coupled to said bispectrum means, for generating an analyte output signal that identifies a characteristic of said chemical analyte if said contour graph corresponds to one of said reference contour graphs from said database created using said positive and negative values for said frequencies $f_1$ and $f_2$.

4. The chemical sensor system as in claim 3, wherein said bispectrum signal substantially represents the bispectrum function:

$$S_{3x}(f_1, f_2) = \sum_{k=-\infty}^{\infty} \sum_{l=-\infty}^{\infty} C_{3x}(k, l)e^{-j2\pi f_1 k}e^{-j2\pi f_2 l},$$

wherein $C_{3x}(k,l)$ is the third-order cummulant of the zero-mean process $x(n)$ represented substantially by the function $C_{3x}(k,l)=E[x(n)x(n+k)x(n+l)]$, where $E[\ ]$ denotes average.

5. A computer apparatus configured with software for use with a chemical sensor system including a metal oxide semiconductor (MOS) gas sensor comprising:
a machine-readable recording medium;
a first instruction means, recorded on said recording medium, for directing said chemical sensor system to generate a fluctuation output signal in response to a plurality of resistance fluctuations of said MOS gas sensor;
a second instruction means capable of calculating the standard deviations of said fluctuation output signal;
a third instruction means for normalizing said fluctuation output signal by dividing said fluctuation output signal by said standard deviation of said fluctuation output signal;
a fourth instruction means, recorded on said recording medium, for directing said chemical sensor system to transform said fluctuation output signal into a bispectrum signal represented by the equation $$S_{3x}(f_1, f_2) = \sum_{k=-\infty}^{\infty} \sum_{l=-\infty}^{\infty} C_{3x}(k, l)e^{-j2\pi f_1 k}e^{-j2\pi f_2 l}$$

using positive and negative values for frequencies $f_1$ and $f_2$;
a fifth instruction means further establishing a contour graph using said positive and negative values for said frequencies $f_1$ and $f_2$ that is representative of the results of said bispectrum signal;
a database of reference contour graphs corresponding to said bispectrum signals using said positive and negative values for said frequencies $f_1$ and $f_2$ of known said analytes; and
a sixth instruction means, recorded on said recording medium, for directing said chemical sensor system to generate an analyte output signal that identifies a characteristic of said chemical analyte if said contour graph established by said fourth instruction means corresponds to a characteristic of one of said reference contour graphs from said database.

6. The computer program product as in claim 5, wherein said bispectrum signal substantially represents the bispectrum function:

$$S_{3x}(f_1, f_2) = \sum_{k=-\infty}^{\infty} \sum_{l=-\infty}^{\infty} C_{3x}(k, l)e^{-j2\pi f_1 k}e^{-j2\pi f_2 l},$$

wherein $C_{3x}(k,l)$ is the third-order cummulant of the zero-mean process $x(n)$ represented substantially by the function $C_{3x}(k,l)=E[x(n)x(n+k)x(n+l)]$, where $E[\ ]$ denotes average.

* * * * *